(12) United States Patent
Armstrong

(10) Patent No.: US 9,724,544 B2
(45) Date of Patent: Aug. 8, 2017

(54) VITAMIN D PROMOTING SUNSCREEN

(75) Inventor: Ernest Armstrong, Palm Desert, CA (US)

(73) Assignee: Ernest T. Armstrong, Palm Desert, CA (US)

( * ) Notice: Subject to any disclaimer, the term of this patent is extended or adjusted under 35 U.S.C. 154(b) by 0 days.

(21) Appl. No.: 13/143,180

(22) PCT Filed: Dec. 21, 2009

(86) PCT No.: PCT/IB2009/055881
§ 371 (c)(1),
(2), (4) Date: Jul. 1, 2011

(87) PCT Pub. No.: WO2010/076731
PCT Pub. Date: Jul. 8, 2010

(65) Prior Publication Data
US 2011/0268678 A1    Nov. 3, 2011

Related U.S. Application Data

(60) Provisional application No. 61/204,146, filed on Jan. 5, 2009.

(51) Int. Cl.
| | | |
|---|---|---|
| *A61K 8/41* | (2006.01) | |
| *A61P 19/00* | (2006.01) | |
| *A61P 19/10* | (2006.01) | |
| *A61P 19/08* | (2006.01) | |
| *A61P 31/04* | (2006.01) | |
| *A61P 31/12* | (2006.01) | |
| *A61P 37/00* | (2006.01) | |
| *A61P 29/00* | (2006.01) | |
| *A61P 35/00* | (2006.01) | |
| *A61P 31/16* | (2006.01) | |
| *A61P 3/10* | (2006.01) | |
| *A61P 3/04* | (2006.01) | |
| *A61Q 17/04* | (2006.01) | |
| *A61K 8/35* | (2006.01) | |
| *A61K 8/37* | (2006.01) | |
| *A61K 8/67* | (2006.01) | |
| *A61K 9/00* | (2006.01) | |
| *A61K 31/00* | (2006.01) | |
| *A61K 31/12* | (2006.01) | |
| *A61K 31/195* | (2006.01) | |
| *A61K 31/4184* | (2006.01) | |
| *A61K 45/06* | (2006.01) | |

(52) U.S. Cl.
CPC .............. *A61Q 17/04* (2013.01); *A61K 8/35* (2013.01); *A61K 8/37* (2013.01); *A61K 8/67* (2013.01); *A61K 9/0014* (2013.01); *A61K 31/00* (2013.01); *A61K 31/12* (2013.01); *A61K 31/195* (2013.01); *A61K 31/4184* (2013.01); *A61K 45/06* (2013.01)

(58) Field of Classification Search
CPC .................................................. A61Q 17/04
USPC ................................................... 424/59
See application file for complete search history.

(56) References Cited

U.S. PATENT DOCUMENTS

| | | | |
|---|---|---|---|
| 5,567,420 A | 10/1996 | McEleney et al. | |
| 5,747,010 A | 5/1998 | Geesin et al. | |
| 6,365,630 B1 | 4/2002 | Fisher et al. | |
| 7,014,842 B2 * | 3/2006 | Dueva-Koganov et al. | ... 424/59 |
| 2004/0057916 A1 * | 3/2004 | Bonda et al. | .............. 424/59 |
| 2004/0081681 A1 | 4/2004 | Vromen | |
| 2004/0091433 A1 | 5/2004 | Buchholz et al. | |
| 2005/0025727 A1 * | 2/2005 | Lott | ........................ 424/59 |
| 2007/0297997 A1 | 12/2007 | Tanner | |
| 2008/0112904 A1 | 5/2008 | Traynor et al. | |

FOREIGN PATENT DOCUMENTS

| | | |
|---|---|---|
| EP | 0313305 A2 | 4/1989 |
| JP | 5-246835 | 9/1993 |
| JP | 2007-077050 | 3/2007 |
| WO | 91/11989 | 7/1993 |
| WO | 2005/082325 | 9/2005 |
| WO | 2006/133828 A1 | 12/2006 |
| WO | WO 2007017179 A1 * | 2/2007 |
| WO | 2007/059091 | 5/2007 |

OTHER PUBLICATIONS

Hume (Hume, E.M. et al., On the Absorption of Vitamin D from the Skin, Biochemical Journal, vol. 21, No. 2, (1927) pp. 362-367; on Jul. 1, 2011 IDS).*
Hume, E.M. et al., On the Absorption of Vitamin D from the Skin, Biochemical Journal, vol. 21, No. 2, pp. 362-367.
Search Report issued in PCT/IB2009/055881 dated Sep. 29, 2010.
De Haes, Petra et al., "1,25-Dihydroxyvitamin D3 and analogues protect primary human keratinocytes against UVB-induced DNA damage," Journal of Photochemistry and Photobiology B: Biology, vol. 78:141-148 (2005).
Pustisek, Nives et al., "A Review of Sunscreens and Their Adverse Reactions," Acta Dermatovenerol Croat., vol. 13 (1):28-35 (2005).
European Supplementary Search Report for Application No. 09836163.7, 11 pages, dated Apr. 18, 2013.

(Continued)

*Primary Examiner* — Bethany Barham
*Assistant Examiner* — Dominic Lazaro
(74) *Attorney, Agent, or Firm* — Nelson Mullins Riley & Scarborough LLP; Jane E. Remillard, Esq.; Jill Gorny Sloper, Esq.

(57) ABSTRACT

A composition suitable for providing protection against ultraviolet radiation containing one or more active ultraviolet radiation absorber through which ultraviolet radiation in approximately the 295 to 315 nanometer range is permitted to enter the skin in an amount sufficient for the body to produce a healthful and disease-opposing quantity of vitamin $D_3$ and chemical precursors thereof. The composition is particularly used in sunscreens promoting on the one hand vitamin $D_3$ production, on the other hand protecting the skin against harmful ultraviolet radiation.

13 Claims, No Drawings

(56) References Cited

OTHER PUBLICATIONS

New Zealand Office Action for Application No. 593932, 3 pages, dated May 3, 2012.
New Zealand Office Action for Application No. 593932, 2 pages, dated Oct. 23, 2013.
New Zealand Office Action for Application No. 616863, 4 pages, dated Oct. 23, 2013.

* cited by examiner

VITAMIN D PROMOTING SUNSCREEN

CROSS REFERENCE TO RELATED APPLICATION

This application claims the priority right from the U.S. provisional patent application 61/204,146 that was filed on Jan. 5, 2009, the content of which is herewith incorporated in its entirety by reference. Also, this application is a national phase entry under 35 U.S.C. §371 based on PCT/IB2009/055881 filed on Dec. 21, 2009.

BACKGROUND OF THE INVENTION

One aspect of the invention is directed to sunscreen formulations that protect the skin against the damaging effects of sunlight while providing the health benefits of increased vitamin D production by the body is disclosed. Another aspect is directed to methods for applying sunscreens.

One example embodiment of the current invention is a sunscreen formulation with active ingredients that screen as much of the damaging, cancer-causing ultraviolet radiation as possible while at the same time permitting passage of light in the wavelengths used by the body to synthesize vitamin D and for tanning.

Sunscreens are widely known and used to prevent the harmful affects of sun exposure. Each different active ingredient used in sunscreens has a unique profile in regard to which wavelengths of ultraviolet (UV) radiation it can absorb and what percentage of those wavelengths it can absorb. Traditionally sunscreen formulators, in their zeal to protect people who are exposed to sunlight from skin cancer and wrinkles, have combine complimentary active ingredients to filter UV radiation in a spectral overlap that screens the broadest spectrum of radiation possible. This broad spectrum approach, unfortunately, also blocks the beneficial wavelengths of radiation in approximately the 295 to 315 nanometer range which are needed for vitamin D synthesis in the skin.

There is broad agreement by vitamin D researchers that getting quantities of vitamin D that are sufficient for optimum health from diet alone is difficult, that vitamin D is produced in sufficient quantities when a sensible amount of sunlight at lower latitudes penetrates the skin and that a large percentage of the population would benefit from higher levels of vitamin D.

Vitamin D plays an essential role in the prevention of bone problems (of which one in twelve people living in higher latitudes is at risk), prevention of some sixteen common cancers (which together are responsible for 30 times more deaths than skin cancer) and modulation of neuromuscular and immune function. Research also indicates that sufficient levels of vitamin D may prevent or reduce the incidence of inflammation, multiple sclerosis, rheumatoid arthritis, hypertension, lupus, cardiovascular disease, type 1 diabetes and type 2 diabetes. Obesity is associated with lower circulating vitamin D levels.

Disclosed are significant, untapped health benefits and considerable commercial potential by the current invention.

Vitamin D is a fat-soluble vitamin that is naturally present in very few foods, added to others, available as a dietary supplement and produced when ultraviolet (UV) rays from sunlight (or tanning beds) enter the skin. Essentially all terrestrial vertebrates, including humans, obtain most of their vitamin D requirement from casual exposure to sunlight. Application of a sunscreen, increased skin pigmentation, aging, hair and clothing all reduce vitamin D production in the skin.

Vitamin D is made in the body when a derivative of cholesterol called 7-dehydrocholesterol is converted to pre-vitamin D3 using the energy from radiation that has entered the skin. Pre-vitamin D3 then spontaneously changes itself into its isomer, vitamin D3. Vitamin D3 is then changed to 25-hydoxyvitamin D3 which circulates in the blood serum or is stored in the liver until needed. 25-hydroxyvitamin D3 is later changed in the kidneys or elsewhere into 1,25-dihydroxyvitamin D3, the main biologically active form.

Following are synonyms: pre-vitamin D3 is cholecalciferol; 25-hydoxyvitamin D3 is 25(OH)D3 or calcidiol; 1,25-dihydroxyvitamin D3 is 1,25(OH)2D3 or calcitriol. in this patent vitamin D stands for vitamin D3, and is sometimes used in a general sense.

The amount of sunscreen (or sunblock) applied to the skin can influence how much of the incoming UV radiation is absorbed, with a thicker layer generally absorbing more radiation. The current invention eliminates certain active ingredients which are known to be sticky or oily, especially in higher concentrations. One advantage of the current invention over traditional sunscreen concoctions is, surprisingly, overall better skin protection because the behavior of sunscreen users is such that they tend to use larger quantities and tend to re-apply more frequently when the ingredients are not as sticky or oily.

The action spectrum of epidermal vitamin D photosynthesis can be graphed in an absorbance curve showing that the peak absorbance for vitamin D synthesis is at about 297 nm, with large amounts produced between 295 and 305 nm, and lesser amounts produced farther from the peak of the curve between 290 and 295 nm and between 305 and 315 nm. (Wavelengths between 270 and 290 nm will cause vitamin D synthesis, but are for the most part filtered by the atmosphere, and therefore generally do not reach the body.) As the wavelengths increase from 290 to 315 nm, so does the relative intensity of UVB radiation reaching the earth's surface. Therefore as a practical matter, it has been discovered that although the absorbance by vitamin D precursors is highest in the 295 to 300 nm range, there is at the surface of the earth a higher intensity of UVB radiation available to the skin between 300 and 305 nm than is available between 295 to 300 nm An important consideration of the current invention is that although the range of radiation that is filtered by the current invention's appropriate UV filter(s) may overlap part of all of the absorption range needed for vitamin D production (i.e. approximately 295 to 315 nm), the active ingredient(s) of the current invention permit the passage of sufficient quantity and quality of radiation for the body to effectively produce vitamin D. The current invention discloses a surprising improvement in sunscreen formulation that teaches away from mainstream full-spectrum screening approach.

Organic molecules known as UV filters (i.e. the active ingredients in sunscreens) have multiple atoms which can vibrate and rotate in relation to each other. Many closely spaced energy transitions mean that instead of absorbing exact frequencies of radiation, molecules absorb groups of frequencies of radiation. The many closely spaced absorption lines combine to make an absorption band. Sunscreens made from organic molecules absorb different percentages of the radiation. These percentages of absorption can be graphed as an absorption curve, with a range (i.e. the shortest to longest wavelengths absorbed) and the peak absorption (i.e. the wavelength which is most highly absorbed). The absorption range and the peak absorption vary by organic molecule. Different organic molecules have differences in how quickly their absorption drops off ("fat" curves as compared to "skinny" curves).

It is important to realize that even within an organic molecule's absorption range, it does not absorb evenly and absorptions near the ends of the range are usually low. Sunscreen manufacturers typically use several active ingredients for screening different parts of the UV spectrum, thereby providing protection from a broad spectrum of radiation.

Factors can influence the determination of the absorbance maximum and other spectral curve data, both for UV filters and vitamin D production, and it should be understood that the overriding essence of the present invention is to permit vitamin D synthesis by the body while blocking out other harmful wavelengths of radiation. For example, 4-aminobenzoic acid (PABA) has a maximum absorbance between 300 and 305 nm in its crystalline form, 289 nm when dissolved in alcohol, and 278 nm when dissolved in water. Therefore, formulations presented in the current invention which include or exclude UV filters based all or in part on the UV filter's absorbance maximum or other spectral curve data are not definitive and are subject to change.

The color of human skin is principally determined by two factors: constitutive pigmentation (which is the genetically-determined color of the skin) and facultative pigmentation (which is an acquired tan). About 72 hours after the skin has been exposed to UVB radiation in approximately the 295 to 315 nm range, a long-lasting base tan (facultative pigmentation) is most noticeable. This delayed tanning is an increase in melanin, through a process called melanogenesis. This invention is a sunscreen that permits the passage of a substantial portion of UVB light in the 295 to 315 nanometer range, thereby permitting the acquisition of a long-lasting base tan while blocking other harmful wavelengths. The sunscreen formulations of the current invention are surprisingly different from all other sunscreens in that those sunscreens filter a broad-spectrum of light, thereby blocking one's ability to get a long-lasting base tan.

Human exposure to UVA radiation has been associated with melanoma, premature aging, sagging, wrinkling skin, sun spots, tanning and immunologic effects. Formulations of the current invention provide substantial screening across the UVA range.

SUMMARY OF THE INVENTION

It is an object of the present invention to create an improved sunscreen promoting tanning and vitamin D generation, while protecting the skin from damage.

This is achieved according to the present invention by a composition suitable for providing protection against ultraviolet radiation containing one or more active ultraviolet radiation absorber through which ultraviolet radiation in approximately the 295 to 315 nanometer range is permitted to enter the skin in an amount sufficient for the body to produce a healthful and disease-opposing quantity of vitamin $D_3$ and chemical precursors and products thereof.

Particularly, this composition may comprises one or two active ingredient that is primarily a UVA filter selected from Avobenzone or Ecamsule and one or more active ingredient that filters ultraviolet radiation in approximately the 295 to 315 nanometer range selected from Octocrylene, Oxybenzone, Octisalate, Sulisobenzone, Homosalate or Merdimate and mixtures thereof, and the weight of the total composition Avobenzone from about 1% to about 5%, Ecamsule 1% to about 10%, Octocrylene 0.5% to about 7%, Oxybenzone 0.5% to about 6%, Octisalate 0.5% to about 6%, Sulisobenzone 0.5% to about 6%, Homosalate 0.5% to about 7% or Merdimate 0.5% to about 5% and mixtures thereof.

DETAILED DESCRIPTION OF THE INVENTION

Samples of vitamin D promoting sunscreen formulations that were manufactured by the inventor in various concentrations were measured using a photospectrometer for their absorption spectra.

Adult humans (two male and two female) have successfully applied the vitamin D promoting sunscreen in various concentrations to their skin prior to exposure to the sun, their initials are: NS, JT, EA, and AG.

Recent research, in part by the inventor, has demonstrated that the body has defenses against the harmful effects of radiation in the vitamin D producing range. When using a sunscreen with one of the current invention's formulations, the user will be protected from unwanted or excess UVB radiation for the following reasons:

One surprising discovery of the current invention is that from a standpoint of protection from UVB radiation, the pre-vitamin D3 absorbance range (i.e. 295 to 315 nm) has a safety advantage over other ranges of UV radiation absorption precisely because of the absorbance by pre-vitamin D3. As such, pre-vitamin D3 can be viewed as not only a chemical with important biological functions but also as a UV filter itself, protecting other biochemicals in its absorbance range. One critical and distinguishing feature of the current invention in regard to the prior art is that others, who are skilled in the art of sunscreen formulation, have consistently over many years recommended overlapping, broad-spectrum active ingredients that effectively filter out radiation in the pre-vitamin D3 absorbance range.

Urocanic acid acts as a natural, endogenous sunscreen or photoprotectant against UVB-induced DNA damage in humans. Urocanic acid is found predominantly in the stratum corneum of the skin. When exposed to UVB irradiation, naturally occurring trans-urocanic acid is converted to the cis isomer, which is known to activate suppressor T cells. The absorbance spectrum of trans-urocanic acid is high in the 260 to 295 range, and moderate in the 295 to 315 nm range.

One surprising discovery of the current invention is that from a standpoint of protection from UVB radiation, Avobenzone's ability to absorb radiation in the 290 to 315 nm range actually increases over time. Since avobenzone is a preferred ingredient, this means that as the sunscreen user spends more time under the sun (i.e. after sufficient vitamin D production has occurred) Avobenzone begins providing better coverage in the 280 to 315 nm range.

"Inactive" ingredients can be a misnomer in that they provide UVB protection in minimal amounts. For example, Polycrylene and Octofluorene can be added to the formulation principally to photostabilize Avobenzone, but in doing so provide some UVB protection.

An unanticipated and surprising advantage of the current invention is that as the vitamin D precursor 1,25(OH)2D3 is produced by the body as a result of invention's formulation, that very 1,25(OH)2D3 protects primary human keratinocytes against UVB-induced DNA damage. (De Haes P, et al., J Photochem Photobiol B. 2005 February 1-; 78(2):141-8.)

DNA's absorbance spectrum shows high absorption between 250 and 265 nm, moderate absorbance between 265 and 290 nm and low to zero absorbance between 290 and 308 nm. In terms of the current invention's sunscreen formulations, those wavelengths permitted to penetrate the skin are generally in the 290 to 315 nm range, a range poorly absorbed by DNA and RNA.

Research has shown that vitamin D has significant protective effects against the development of cancer because it regulates cells growth, cell differentiation and cell death. Vitamin D works by binding to a receptor in cells. Researchers in Italy identified a possible link between melanoma and a gene involved in vitamin D metabolism. (Cancer, Nov. 1, 2008) Genetic differences in the vitamin D receptor gene BsmI mean that people may have different levels of vitamin D in their bodies, and some people may have more vitamin D-related protection against cancer than others. According to the study's authors, these findings indirectly support the hypothesis that sun exposure might have an anti-melanoma effect through activation of the vitamin D system.

The above safety considerations of the current invention's formulations are surprising improvements over broad-spectrum sunscreen formulations.

It is a contention of the current invention that prior art teachings and expectations regarding direct sunlight are flawed and at best imperfect; and that the current invention provides a surprising and unanticipated improvement over all of this art.

Some formulations of the current invention exclude active ingredients (UV filters) which block a high percentage of those wavelengths of UV radiation used by the body to manufacture vitamin D and include active ingredients which permit the passage of a high percentage of the UV radiation used to manufacture vitamin D. In essence, some embodiments of the current invention anticipate an optimal balance of providing protection from the negative effects of solar radiation or tanning bed radiation while permitting a sufficient amount of vitamin D production by the body, thus providing the best of both worlds.

One embodiment of the current invention using an actual product, one example commercial sunscreen has four active ingredients: Homosalate, Avobenzone, Octinoxate and Octisalate. An example formulation of the current invention would include as active ingredients only Homosalate, Avobenzone and Octisalate (because they individually and in combination with one another block only a fraction of the UV radiation needed for vitamin D synthesis) but would substantially exclude Octinoxate (because Octinoxate itself blocks a large percentage of the UV radiation needed for vitamin D synthesis. However, trace amounts of Octinoxate may be present).

Following are examples of combinations of active ingredients which are appropriate for different embodiments of the current invention (there are many more combinations possible, and this list is for purposes of demonstration only): Sulisobenzone, Avobenzone, Homosalate and Octisalate; Avobenzone, Homosalate and Octisalate; Sulisobenzone, Avobenzone and Homosalate; Sulisobenzone, Avobenzone and Octisalate; Sulisobenzone and Avobenzone; Avobenzone and Homosalate; as well as Avobenzone and Octisalate.

In one combination of the invention, Sulisobenzone, Homosalate and Octisalate are each used in lower concentrations (5 percent or less because they absorb minimal UVB radiation); and Avobenzone in a higher concentration (3 to 5 percent, the maximum permitted by law).

In another combination, Homosalate and Octisalate are each used in lower concentrations (5 percent or less because they absorb minimal UVB radiation); and Avobenzone in a higher concentration (3 to 5 percent, the maximum permitted by law).

In another combination, Homosalate and Octisalate are each used in lower concentrations (5 percent or less because they absorb minimal UVB radiation); Avobenzone in a higher concentration (3 to 5 percent, the maximum permitted by law) and Ecamsule in a higher concentration (3 to 10 percent, the maximum permitted by law).

Aspects of some embodiments of the current invention thereby teach away from the long-established mantra of "broad-spectrum" sunlight blocking and achieve surprising and valuable benefits. Some aspects of the current invention describe a safe, user-friendly and pragmatic solution to the problem of preventing vitamin D production in the skin by broad-spectrum sunscreens.

The appropriate UV filters considered acceptable for inclusion in examples of the current invention's formulations, either alone or in combination with any number of other appropriate UV filters, include, but are not limited to, the following examples of UV filters which absorb little or no UV radiation in the vitamin D producing range:

Selected from the Class of Anthranilates:

Example 1.) Meradimate (also known as menthyl anthranilate, MA, methyl 2-aminobenzoate or carbomethoxyaniline, CAS #: 134-09-8), is an ester of anthranilic acid. Meradimate has an absorption maximum (peak) between 336 and 340 nm, an absorption range between 260 and 380 nm and a critical wavelength (CW) of 363 nm. Because of its relative lack of absorption in the vitamin D producing range, Meradimate is appropriate as an ingredient in the current invention.

Selected from the Class of Benzophenones:

Example 2.) Sulisobenzone (also known as Benzophenone-4, Escaiol 577, Uvinul MS 40 or 2-hydroxy-4-methoxybenzophenone-5-sulfonic acid, CAS #: 4065-45-6) is an ingredient in some sunscreens. Sulisobenzone has an absorption range from 260 to 375 nm. Because of its minimal to somewhat moderate absorption in the vitamin D producing range, Sulisobenzone is generally appropriate as an ingredient in the current invention.

Example 3.) Uvinul A Plus (also known as diethylamino hydroxybenzoyl hexyl benzoate or DHHB, CAS #302776-68-7) is used in sunscreens. Uvinul A Plus has absorption maxima at about 210 nm and in the 354 to 357 nm range.

Because of its relative lack of absorption in the vitamin D producing range, Uvinul A Plus is appropriate as an ingredient in the current invention.

Example 4.) Benzophenone-9 (also known as 2,2'-dihydroxy-4,4'-dimethoxybenzophenone-5,5'-disodium sulfonate, 2,2″-dihydroxy-4,4'-dfmethoxybenzophenone-5,5'-disulfonic acid sodium salt or Uvinul D 49, CAS #: 76656-36-5). Because of its relative lack of absorption in the vitamin D producing range, Benzophenone-9 is appropriate as an ingredient in the current invention.

Example 5.) Oxybenzone (also known as 2-hydroxy-4-methoxybenzophenone, Benzophenone-3, Uvinul M 40, Eusolex 4360 or Escalol 567, CAS #: 131-57-7) is used in sunscreens. Oxybenzone has an absorption range of 270 to 350 nm and maxima absorption at 289 nm and at 329 nm. Oxybenzone has a critical wavelength (CW) of 361 nm. Because its absorption in the vitamin D producing range is minimal to moderate, Oxybenzone is marginally appropriate as an ingredient in the current invention. If included, a low concentration is preferred.

Example 6.) Mexenon (also known as 2-hydroxy-4-methoxy-4'-methyl-benzophenone, Benzophenone-10 or Mexenone, CAS #: 1641-17-4) is used in sunscreens.

Because its absorption in the vitamin D producing range is minimal to moderate, Mexenon is appropriate as an ingredient in the current invention. If included, a low concentration is preferred.

Selected from the Class of Camphors:

Example 7.) Ecamsule (also known as Mexoryi SX, terephthalylidene dicamphor sulfonic acid or TDSA, CAS #: 90457-82-2) is in sunscreens by L'Oreal. Ecamsule has a maximum absorbance at 345 nm, provides strong protection in the 320 to 340 nm range, and weak protection farther out in the fringes in the 290 to 400 nm range. Because it exhibits only minor absorption in the vitamin D producing range, Ecamsule is appropriate as an ingredient in the current invention.

Selected from the Class of Cinnamates:

Example 8.) Octocrylene (also known as Uvinul N 539 T, 2-ethylhexyl alpha-cyano-beta-phenylcinnamate, alpha-cyano-beta-phenylcinnamate or Parsol MCX, CAS #: 6197-30-4) is used as an ingredient in sunscreens. Octocrylene can stabilize Avobenzone. Octocrylene has an absorption range from 250 to 360 nm and a maximum absorption at 303 nm. Octocrylene has a critical wavelength (CW) of 356 nm. Because its absorption in the vitamin D producing range is minimal to moderate, octocrylene is marginally appropriate as an ingredient in the current invention. If included, a low concentration is preferred.

Selected from the Class of Dibenzoylmethanes:

Example 9.) Avobenzone (otherwise known as 4-tert-butyl-4'-methoxy-dibenzoylmethane, Parsol 1789, Eusolex 9020, Escalol 517, Neo Heliopan 357, Uvinul BMDM or butyl methoxydibenzoylmethane, CAS #: 70356-09-1) is an ingredient used in sunscreens. It can exhibit photoinstability. Avobenzone has an absorption range between 320 and 390 nm and a maximum absorption of radiation at 360 nm and a critical wavelength (CW) of 383 nm. Because of its relative lack of absorption in the vitamin D producing range, Avobenzone is appropriate as an ingredient in the current invention.

Example 10.) Eusolex 8020 (also known as Eusolex-8020, 4-isopropyl-dibenzoylmethane, 4-isopropyldibenzoylmethane or propyl dibenzoylmethane, CAS #: 63250-25-9) is used in sunscreens. Some manufacturers have withdrawn it from the market. Because of its relative lack of absorption in the vitamin D producing range, Eusolex 8020 is appropriate as an ingredient in the current invention.

Selected from Hybrids:

Example 11.) Polysilicone-15 (also known as BMP, dimethico-diethyibenzal malonate, dimethicodiethylbenzal malonate, or Parsol SLX, CAS #: 207574-74-1) is used in sunscreens. Because of its relative lack of absorption in the vitamin D producing range, Polysilicone-15 is appropriate as an ingredient in the current invention.

Selected from the Class of Imidazoles: Example 12.) Bisdisulizole disodium (also known as Neo Heliopan AP, disodium phenyl dibenzimidazole tetrasulfonate, bisimidazylate, DPDT or Bisymidazylate, CAS #: 180898-37-7) is added to sunscreens. Bisdisulizole disodium has an absorption range from 300 to 365 nm and a maximum absorption at 335 nm. Because of its relative lack of absorption in the vitamin D producing range, Bisdisulizole disodium is appropriate as an ingredient in the current invention.

Selected from the Class of p-Aminobenzoic Acids:

Example 13.) PEG-25 PABA (also known as 4-Bis(polyethoxy)para-aminobenzoic acid polyethoxyethyl ester, p-Aminobenzoic acid or Uvinul P 25, CAS #: 116242-27-4). Because of its minimal absorption in the vitamin D producing range, PEG-25 PABA is appropriate as an ingredient in the current invention.

Selected from the Class of Salicylates:

Example 14.) Homosalate (also known as 3,3,5-trimethylcyclohexyl salicylate, CAS #: 118-56-9) is used in sunscreens. Homosalate has higher absorption of ultraviolet radiation in the 300 to 312 nm range, and has a critical wavelength (CW) of 328 nm. Because its absorption in the vitamin D producing range is minimal to moderate, Homosalate is marginally appropriate as an ingredient in the current invention. If included, a low concentration is preferred.

Example 15.) Octisalate (also known as Octyl Salicylate, Escalol 587 or 2-ethylhexyl salicylate, CAS #: 118-60-5) is an ingredient in sunscreens. Octisalate has maximum absorption of radiation between about 305 and 307 nm, an absorption range between 280 and 320 nm, and a critical wavelength (CW) of 327 nm. Because its absorption in the vitamin D producing range is minimal to moderate, Octisalate is marginally appropriate as an ingredient in the current invention. If included, a low concentration is preferred.

The examples of UV filters (i.e. active sunscreen ingredients) that are included as appropriate active ingredients are herein meant to be representative and certainly the current invention contemplates the inclusion of any molecule based on its ability to fully or partially permit the passage into the skin of UV radiation in approximately the 295 to 315 nm range.

Note that the terms "excluded" and "inappropriate for inclusion" used herein are intended to mean that there is 0 percent concentration, or that there is some small, trace, substantially ineffective amount present—with examples including less than 0.1% (wt.), less than 0.05% (wt.), less than 0.01% (wt), less than 0.25% (wt), or less than 0,001% (wt). The inappropriate UV filters which are to be excluded from the current invention's formulations, include, but are not limited to, the following UV filters demonstrating a high percentage of the UV radiation absorption in the vitamin D producing range: Benzophenone (CAS #: 119-61-9); 2,4-Dihydroxybenzophenone (Benzophenone-1, CAS #: 131-56-6); $2,2^1,4,4'$-Tetrahydroxybenzophenone (Benzophenone-2 or Uvinul D 50, CAS #: 131-55-5); 2,2'-Dihydroxy-4,4'-dimethoxybenzophenone (Benzophenone-6, CAS #: 131-54-4); 2,2'-Dihydroxy-4-methoxybenzophenone (Benzophenone-8, Dioxybenzone, CAS #: 131-53-3); 2-Hydroxy-4-(Octyloxy)Benzophenone (Benzophenone-12, Octabenzone, CAS #: 1843-05-6); 4-Methylbenzylidene camphor (also known as 4-MBC, Uvinul MBC 95, Enzacamene, Eusolex 6300, Parsol 5000 or 3-(4-methylbenzyliden)camphor, CAS #: 36861-47-9); Cinoxate (also known as 2-ethoxyethyl p-methoxycinnamate, CAS #: 104-28-9); Octinoxate (also known as octyl methoxycinnamate, OMC, Uvinul MC 80, Neo Heliopan AV, Parsol MCX or ethylhexyl methoxycinnamate, CAS #: 5466-77-3); Diethanolamine p-methoxycinnamate (also known as Diethanolamine methoxycinnamate or DEA methoxycinnamate, CAS #: 56265-46-4); Isoamyl p-methoxycinnamate (also known as, Isopentenyl-4-methoxycinnamate, IMC, Neo Heliopan E1000 or Amiloxate, CAS #: 71617-10-2); Dibenzoylmethane (also known as clibenzoyl methane, CAS #: 120-46-7); Bisoctrizole (also known as Tinosorb M, methylene bis-benzotriazolyl tetramethyl butyl phenol or MBBT, CAS #103597-45-1); Zinc oxide (also known as ZnO); Titanium dioxide (also known as titanium (IV) oxide, $TiO_2$ or titania); Cerium((V) oxide (also known as ceria, cerium oxide or CeO2); Ensulizole (also known as phenyl benzimidazole sulfonic acid, phenylbenzimidazole, 2-phenylbenzimidazole-5-sufonic acid, PBSA, Parsoi HS, CAS #: 27503-81-7); Aminobenzoic acid (also known as 4-aminobenzoic acid, p-aminobenzoic acid or PABA, CAS #: 150-13-0); Padimate-0 (otherwise known as Padimate O, Ethylhexyl dimethyl PABA, 2-ethylhexyl 4-dimethylaminobenzoate, Escalol 507, octyl dimethyl PABA or OD-PABA, CAS #: 21245-02-3); Padimate-A (also known as amyl p-dimethylaminobenzoate, amyl paradimethylaminobenzoate or amyl dimethyl PABA, CAS #21245-01-2.); Glyceryl Aminobenzoate (also known as glyceryl p-aminobenzoate, glyceryl PABA, glyceryl 1-(4-aminobenzoate), monoglyceryl ester or Lisadimate, CAS #: 136-44-7); Ethylhexyl Triazone (also known as Octyl Triazone, ethylhexyl triazone, Uvinul T 150 or ET, CAS #: 88122-99-0); Trolamine Salicylate (also known as triethanolamine salicylate or TEA salicylate, CAS #: 002174-16-5); Drometrizole Trisiloxane (also known as DTS, Mexoryl XL, CAS #: 155633-54-8); Bemotrizinol (also known as Tinosorb S, bis-ethylhexyloxyphenol methoxyphenyl triazine, bis(ethylhexyloxyphenol methoxyphenol) triazine, BEMT or Anisotriazine, CAS #: 187393-00-6); Iscotrizinol (also known as Uvasorb HEB, diethylhexyl butamido triazone, dioctyl butamido triazone or DBT, CAS #: 154702-15-5); and Digalloyl trioleate (otherwise known as 5-(3,3-Di methyl 2 norbornyliden)-3penten-2-one, CAS #17048-39-4). Because of their absorption in the vitamin D producing range the compounds of the formula I as described in US Pub. No.: 2004/0091433 A1 are also inappropriate as ingredients in the current invention.

The examples of UV filters that are excluded as inappropriate active ingredients (noting again that some small, trace and ineffective amount may be present) are herein meant to be representative and certainly the current invention contemplates the exclusion of any molecule based on its ability to fully or amply block the passage into skin of UV radiation in approximate the 295 to 315 nm range. Other UV filters are listed as substances in the CTFA International Cosmetic Ingredient Dictionary, or are approved by the appropriate regulatory agencies in Australia, Canada, China, EU, Japan, Sweden, The Netherlands, UK or USA; or are cleared by the US Cosmetic Ingredient Review (CIR) group, all of which are which is incorporated in the current invention by way of reference.

The following representative examples of ingredients may or may not be selected as appropriate for inclusion in the present invention, with one determining factor being an absorbance curve with an amplitude and breadth that permit sufficient radiation in the vitamin D producing range (approximately 295 to 315 nm) to enter the skin thereby producing a healthful, disease-opposing amount of vitamin D: 2-(2-Hydroxy-5-methyl-phenyl)Benzotriazole (Drometrizole, CAS #: 2440-22-4); 2-Hydroxy-4-methoxybenzophenone-5-sulfonic Acid, Monosodium Salt (Benzophenone 5, CAS #: 6628-37-1); 2-Hydroxyethyl salicylate (CAS #: 87-28-5); 3-Benzylidene camphor, (also known as 3BC, CAS #15087-24-8); 3-[2-(4-diethylaminophenyl)-2-oxoethyl]thiazolium salt; 5-Chloro-2-hydroxybenzophenone (Benzophenone-7, CAS #: 85-19-8); Aesculetin (also known as esculetin, 6,7-dihydroxycoumarin and cichorigenin); Artemia salina plankton extract, Benzophenone-5 (also known as Benzenesulfonic acid, CAS#6628-37-1); Benzyl salicylate (CAS #: 118-58-1); Benzylidene Camphor Sulfonic Acid (CAS #: 56039-58-8); Beta, 2-glucopyranoxy propyl hydroxy benzophenone; Bis(2,4-ihydroxyphenyi) Methanone (Benzophenone-11, Benzophenone-n, Uvinul M 493,CAS #: 1341-54-4); Bornelone (CAS #: 2226-11-1); Broccoli sprout extracts including sulforaphane; brown algae polyphenols (BAPs), Camphor benzalkonium methosulfate, (also known as Mexoryl $SO_1$ CAS#52793-97-2); Dibenzoylmethane (CAS #: 120-46-7); Dibenzylideneacetone (also known as dibenzalacetone or dba); Dihydroxyacetone; Diisopropyl methyl cinnamate (CAS #32580-71-5); Dimethicodiethylbenzal mafonate; Dimethoxyphenyl-[1-(3,4)]-4,4 dimethyl 1,3 pentanedione; Dipropylene glycol salicylate; Diurethane dimethacrylat$\theta$ (CAS #: 103597-45-1); Endocannabinoids; Ethyl 2-cyano-3,3-diphenylacrylate (Etocrilene, CAS #: 5232-99-5); Ethyl 4-[bis(hydroxyl propyl)] aminobenzoate (also known as propoxylate of p-aminoethylbenzoate or Roxadimate, CAS #: 58882-17-0); Ethyl Cinnamate (CAS #: 103-36-6); Ethyl dihydroxypropyl PABA; Ethyl Diisopropylcinnamate (CAS #: 32580-72-6); Ethyl Methoxycinnamate (CAS #: 99880-64-5); Ethyl PABA (also known as benzocaine); Ethyl Urocanate (CAS #: 27538-35-8); Ethylhexyl dimethoxy benzylidene dioxoimidazoline propionate; Ferulic acid; Forskolin; Glyceryl ethylhexanoate dimethoxycinnamate; Glyceryl octanoate dimethoxycinnamate; Isopropylbenzyl Salicylate (CAS #: 94134-93-7); Isopentyl trimethoxycinnamate trisiloxane; Isopropyl methoxycinnamate(CAS #: 5466-76-2); Lawsone; Magnesium aluminum silicate, Menthyl salicylate (CAS #: 89-46-3); p-Aminobenzoic Acid, 2,4-dihydroxy-N-(3-hydroxypropyl)-3,3-dimethylbutanimide ester; Petrolatum jelly (CAS #: 8009-03-8); Phenylbenzimidazole; Phenylbenzimidazole Tea sulfonate (CAS #: 73705-00-7); Polyacrylamido methylbenzylidene camphor (CAS #113783-61-2); Quicksun Clear and Quicksun Matte extracts; Salicylic acid; Sodium Phenylbenzimidazole sulfonate (CAS #: 5997-53-5); Sorbohydroxamic acid; Umbelliferone (also known as 7-hydroxycoumarin); and Urocanic Acid (4-Imidazoleacrylic acid, CAS #: 104-98-3) and each of their respective metabolites, acids, hydroxyl groups, esters, salts, alcohols, acyl groups, related chemical species, pharmaceutically-acceptable salts thereof and the like.

Additional organic screening agents may be selected for said inclusion especially from: the anthranilates, benzylidenecamphors, benzimidazoles, benzotriazoles, cinnamates, dibenzoylmethanes, imidazolines, PABAs, salicylates, triazines and nucleic acids including DNA and RNA.

In addition to the specific examples of UV filters provided as appropriate or inappropriate for inclusion in the present invention's formulations are each of their respective metabolites, acids, hydroxyl groups, esters, salts, alcohols, acyl groups, related chemical species, pharmaceutically-acceptable salts thereof and the like.

There are various factors that one must consider when selecting the appropriate active and inactive ingredients for the current invention, remembering always that the guiding light in that decision is always a balance between making it possible for the body to manufacture an adequate amount of vitamin D and preventing excessive adverse effects to the skin from the sun. Those factors involved in the selection of appropriate ingredients include, but are not limited to, the following. Study reports presenting the UV radiation absorbance ranges and maxima (i.e. molar absorbance coefficients) for the active ingredients, inactive ingredients and vitamin D production can vary depending upon which solvent medium (e.g. water, methanol, acetonitrile, n-hexane) is used when the molecule's spectral data is collected, the type of the spectrophotometric measurements, the calibration of the instrumentation, pollutants in the samples, the pH of the samples, water-in-oil, oil-in-water, the examination in vivo or in vitro, the concentration of the molecule, the length of time the molecule was been exposed to radiation, the presence or absence of other molecules, the intensity of radiation to which the active ingredient has been exposed, the degradation of the molecule, skin types, the presence or absence of SPF boosters such as glass beads, UV-Pearls and microcapsules or ingredients to improve photostability such as antioxidants and Triplet-Triplet Quenches, and the interpretation of the data. The current invention acknowledges that not all people applying sunscreen apply it as thickly as others, and that generally the thicker it is applied, the better the UV protection. It has been reported that sunscreen users on average apply a layer of sunscreen that is only one forth of the recommended thickness. Generally the thickness is measured in layers 2, 1 and 0.5 mg/cm2 deep. This thickness question could affect the inclusion or exclusion decision. Such differences could conceivably influence the decision to include or exclude the UV filter candidate, any such change from the inclusionary list to the exclusionary list (or vice-versa) is contemplated by the current invention without detracting from the essence. For example, shifts in the absorbance curves for oxybenzone, TDSA and Bisdisulizole disodium have been reported as a result of the base (TEA or NaOH) used to neutralize the sample.

The concentrations of each of the active ingredients in the current invention can vary, resulting in SPF numbers from 2 to 50 plus reflecting the product's ability to protect from sunburn (erythema) and low, medium, high or highest "Star" (or other rating) to reflect its ability to block UVA radiation; the essential being that the concentrations permit the synthesis of at least a health-promoting amount of vitamin D.

In addition to sunscreens, whose primary purpose is medicinal sunscreening (preventing UV radiation from harming the skin), the current invention can be applied to making the therapeutic claim that is does not prevent vitamin D production in cosmetic products including but not limited to hair products, lip balms, creams, lotions, sprays, insect repellants and make-up which often also include a UV filter.

There are wavelengths of radiation other than approximately 295 to 315 nm (those in the vitamin D range) which can be beneficial to the body as well.

Depending on the formulation, the current patent can include or exclude active ingredients in order to permit other health-enhancing wavelengths to enter the skin.

In one embodiment of a method of the invention, a vitamin D enhancing sunscreen with a formulation as per the current invention is applied to the skin first, and then, if the sunscreen user desires to remain in the sun for an extended exposure (i.e. long enough to potentially induce erythema), the person may then apply a second or third coat of sunscreen which contains UVB blocking ingredients herein defined as inappropriate for vitamin D production. The result being that by the time of the second application, the body will have already produced sufficient vitamin D for proper health for the day. The period of time before applying the second sunscreen should be sufficient to allow an effective amount of Vitamin D to be absorbed. Examples include at least about 10 minutes, at least about 20 minutes, at least about 30 minutes, and at least about 1 hour.

In one embodiment, a vitamin D enhancing sunscreen with a formulation as per the current invention is applied to certain areas of the body at the same time as an additional sunscreen which has UVB blocking ingredients (and perhaps other inactive ingredients such as moisturizers) herein defined as inappropriate is applied to other areas. For example, a sunscreen user may wish to use a sunscreen with inappropriate ingredients on his or her face at the same time as a sunscreen with only appropriate ingredients on his or her arms and legs.

The current invention may be specially formulated for use on humans of different ages, with increased vitamin D production especially preferred in the elderly, and certain considerations such as waterproof for children.

The current invention may be formulated for use on domestic animals such as horses, dogs and cats; and on farm animals. Increasing vitamin D levels in farm animals such as cows, pigs and goats provides health benefits to the farm animals and, surprisingly, increases the vitamin D content of their milk and meat, a health benefit to the humans who consume them.

Some embodiments of the present invention are for adults, others for children and embodiments may be formulated as a lotion, cream, gels, oil, spray, emulsion, solution, moisturizer, ointment, transdermal delivery system for other molecules, make-up, foundation, shampoo, soap, spray, stick, lip balm and the like; can be made sticky, non-sticky, waterproof, water resistant, abrasion resistant or rub-proof, rinse-off, leave-on and the like; and can contain humectants, emulsifiers, emollients, preservatives and thickeners and the like. Other sunscreen ingredients may include anti-irritants, and products which help cell communication (signaling), and which mimic the structure and function of the skin.

The antioxidants or free-radical scavengers that may be used in the composition according to the invention comprise, besides certain anti-pollution agents mentioned above, vitamin E and its derivatives such as tocopheryl acetate; vitamin C, panthenol (provitamin B5), retinyl palmitate (vitamin A palmitate), bioflavonoids; coenzyme Q10 or ubiquinone; certain enzymes, for instance catalase, superoxide dismutase, lactoperoxidase, glutathione peroxidase and quinone reductases; glutathione; benzylidenecamphor; benzylcyclanones; substituted napthalenones; pidolates; phytanetriol; gamma-oryzanol; lignans; and melatonin as well as all of their respective salts, analogues and metabolites.

In one embodiment, Spectrasolv technology is used to formulate the dielectric constant of the oil phase to that at which Avobenzone is made most stable. In one preferred embodiment, Avobenzone is photostabilized with Octofluorene by Hallstar or other manufacturer. At use levels of 1 to 2 percent, Octofluorene absorbs UV radiation in such minimal amounts as not to affect SPF or vitamin D synthesis, and its absorbance spectrum fits well in that most of its absorption is in the UVA range. In one preferred embodiment, Avobenzone is photostabilized and made water resistant with Polycrylene (INCI Name: Polyester-8 and CAS: 862993-96-2) by Hallstar or other manufacturer. At use levels of 1 to 2 percent, Polycrylene absorbs UV radiation in such minimal amounts as not to affect SPF or vitamin D synthesis. Polycrylene also improves the substantivity of sunscreen formulations as measured by resistance to wash-off. In one preferred embodiment, Avobenzone is photostabilized using Hawaiian Tropic's SunSure proprietary combination of ingredients.

In addition to the particular molecules presented in lists of UV filters (both appropriate and inappropriate); the current patent contemplates the inclusion or exclusion of their respective metabolites, acids, hydroxyl groups, esters, salts, alcohols, acyl groups, pharmaceutically acceptable carriers, and other related chemical species thereof.

In one preferred embodiment, a UV booster for organic sunscreen actives such as the citrate ester Trimollient BC (INCI: Tris PPG-3 benzyl citrate) provides benefits in sun protection.

Some ingredients which are somewhat erroneously referred to as "inactive" ingredients in sunscreens, for example unrefined shea butter, coconut oil and other oils, are known to have mild UV blocking properties. The following ingredients, (with others possible in keeping with the vitamin D enhancing teachings of the current invention), may or may not be included in the formulation of the current invention based partially on their absorbance or non-absorbance of radiation in the range that produces vitamin D: Acrylates; C10-30 alkyl acrylate crosspolymer; alcohol (ethyl-, isobutyl-, isopropyl-, methyl-, prop-, and butyl-alcohol or other alcohols), allantoin; allantoin-p-aminobenzoic acid complex p-aminobenzoic acid; aluminum; aloe vera leaf juice; aloe vera; aloe barbadensis leaf juice; alumina; amyl acetate; amyl dimethyl PABA; amyl para-dimethylaminobenzoate; amyi-p-dimethylaminobenzoate; antibacterial agents; antifungal agents; antioxidants; aromatic amino acids (such as phenylalanine; tryptophan; and tyrosine); ascorbyl palmitate; Baobab pulp; beeswax; benzyl alcohol; BHA; BHT; 2-bromo-2-nitropropane-1; 3-diol; buffers such as PBS or HEPES; borage seed oil; carrot oil; camphor; caprylic/capric triglyceride; Carbomer 934; carboset; cellulose gum; cetyl alcohol; cetyl palmitate; cetyl stearyl glycol; cetearyl alcohol; cetyl alcohol; cetyl PEG/PPG-10/1 dimethicone; cinoxate citric acid; clove oil; co-enzyme Q10; cocoa butter; coconut oil; collagen; colorants; controlled release agents; Coolact 10 (INCI: Menthoxypropanediol); creatine; dasheen root extract; dielectric spheres; dihydroxyacetone (self-tanning ingredient); diazolidinyl urea; dibutyl adipate; disodium EDTA; dimethicone; 5-(3; 3-dimethyl-2-norbornyliden)-3-penten2-one; 3; 4-dimethyl-phenyl-glyoxylic acid sodium salt; dimethyl polysiloxane; dipropylene glycol salicylate; DMSO; dyes; edelweiss; elastin; emollients; Emu oil; Emulium Kappa; ethyl alcohol; 2-ethylhexyl 4-phenylbenzophenone-2-carboxylic acid; ethylhexyl palmitate; ethylenediamine; eucalyptus leaf oil; ferulic soy glycerides (FSG); fruit extracts (such as guava; mango; papaya; passionflower); FD&C yellow No. 5; FD&C red No. 4; fragrances; galactoarabinan; glycerin; glyceryl PABA; glyceryl stearate; hemp seed oil; hydroxyacetone (self-tanning ingredient); isohexadecane; isopropyl myristate; isopropyi palmitate; jojoba oil; kukui nut (seed) extract; lanolin; lanoiin alcohol; lanolin derivatives; lanolin oil; lawsone (2-hydroxy-1; 4-naphthoquinone); magnesium aluminum silicate; menthol; metallic pigments; microcapsules such as UV-Pearls; microcrystalline titanium coated mica platelets; microcrystalline wax; mircospheres; mineral oil; neopentyl glycol; oleth-3; oleth-3-phosphate; C30-38 olefin/isopropyl maleate/MA copolymer; ozokerite; panthenol; parabens (ethyl-; isobutyl; isopropyl-; methyl-; prop-; and butyl-propylparabens); Padina extract; paraffin; PEG 2 stearate; PEG-8; penetration enhancers (such as terpenes and terpenoids); perfumes; petrolatum; phenoxy-ethanol; phenoxyethanol; 2-phenylbenzimidazole; photostability improvers such as Corapan TQ (diethylhexyl 2; 6-naphthalate) and Triplet-Triplet Quenches; polymers (including polymers to assist in dispersion and rheology); propylene glycol; polyoxyl-40-stearate; plumeria extract; polysorbate 60; propellant 46; propellant 12/114; propoxylate of p-aminoethylbenzoate; propylparaben; propylene glycol; propylene glycol stearate; proteins (such as proteins which are rich in aromatic amino acids such as keratin and albumin); Quaternium 15; red petrolatum; retinoic acid; retinol; rice extract; rose petal extract; safflower seed oil (Hydresia); SD alcohol 40; SPF boosters such as glass beads; sesame oil; shea butter; silaca sodium carbomer; sodium ascorbyl phosphate; sodium cetearyl sulfate; sodium citrate; sodium chloride; sodium hydroxide; sorbitan oleate; sorbitan stearate; sorbitol; stabilized aloe vera gei; stearic acid; stearyl alcohol; stearyl hydrogenated dimmer dilinoleate copolymer; sunflower oil; synthetic spermaceti; *theobroma cacao* (cocoa) seed butter; tocopheryl acetate; triethanolamine stearate; vitamins such as A; C; E; D; B3; B6; B12; water; watermelon (*Citrullus lanatus*); wax; wheat (triticum vulgare); wolfberry (goji berry); germ oil; X-Tend™ 226 (a polar ester with high-solubilizing capacity for Oxybenzone and Avobenzone); xanthan gum; and each of their respective metabolites, acids, hydroxyl groups, esters, salts, alcohols, acyl groups, related chemical species, pharmaceutically-acceptable salts thereof and the like.

When considering the various embodiments of the invention described herein, those knowledgeable in the art will appreciate that these are illustrative only. Such embodiments do not limit the scope of the invention. Those knowledgeable in the art involved will appreciate that many variations, substitutions, equivalents, and like modifications may be made within the scope of the present invention.

What is claimed is:

1. A topical composition comprising:
    a) one or more ultraviolet radiation (UVR) filtering agents selected from the group consisting of ultraviolet A (UVA) radiation filtering agents avobenzone, diethylamino hydroxybenzoyl hexyl benzoate, meradimate and ecamsule; and
    b) at least one UVR filtering agent selected from the group consisting of ultraviolet B (UVB) radiation filtering agents octocrylene at a concentration from 0.5% to 7% (wt), oxybenzone at a concentration from 0.9% to 3.6% (wt), octisalate at a concentration from 1.1% to 4.2% (wt), benzophenone-4 at a concentration of 5% (wt) or less and homosalate at a concentration of 0.5% to 7% (wt), wherein:
the UVR filtering agents are present in the composition in an amount effective to filter UVA when the composition is applied to the skin of a human exposed to UVR;
the composition allows passage of 25% or more of the UVR in the 295 nm to 315 nm range when applied to the skin in the amounts of between 0.01 and 50 milligrams per square centimeter;
the composition allows passage of radiation in the approximately 295 to 315 nm range to permit production of vitamin D when the composition is applied to the skin of a human exposed to UVR;
and the composition does not include zinc oxide at a concentration of 0.25% (wt) or more, titanium oxide at a concentration of 0.25% (wt) or more, or cerium oxide at a concentration of 0.25% (wt) or more.

2. The topical composition of claim 1, wherein, when the composition is applied to the skin, the composition reduces or inhibits the induction of erythema in the skin.

3. The topical composition of claim 1, wherein, when the composition is applied to the skin, the composition permits facultative pigmentation of the skin.

4. The topical composition of claim 1, wherein the composition comprises octisalate at a concentration of between 1.1% and 4.2% (wt).

5. The topical composition of claim 1, wherein the composition comprises oxybenzone at a concentration of between 0.9% and 3.6% (wt).

6. The topical composition of claim 1, wherein the composition comprises avobenzone at a concentration of between 1% and 5% (wt).

7. The topical composition of claim 1, wherein the composition comprises homosalate at a concentration of between 0.5% and 7% (wt).

8. The topical composition of claim 1, wherein the composition comprises benzophenone-4 at a concentration of 5% or less (wt).

9. The topical composition of claim 1, wherein the composition comprises octocrylene at a concentration of between 0.5% and 7% (wt).

10. The topical composition of claim 1, wherein the composition does not comprise any of the UVR filtering agents selected from the group consisting of: benzophenone-8, cinoxate, octinoxate, isopentenyl-4-methoxycinnamate, bisoctrizole, titanium dioxide, ensulizole, ethylhexyl 4-dimethyl p-aminobenzoate, ethylhexyl triazone, triethanolamine salicylate, drometrizole trisiloxane, bemotrizinol, benzophenone, 2,4-dihydroxybenzophenone, 2,2',4,4'-tetrahydroxybenzophenone, 2,2'-dihydroxy-4,4'-dimethoxybenzophenone, 2,2'-dihydroxy-4-methoxybenzophenone, 2-hydroxy-4-(octyloxy)benzophenone, 4-methyibenzylidene camphor, diethanolamine p-methoxycinnamate, isoamyl p-methoxycinnamate, cerium(IV), aminobenzoic acid, Padimate-A, glyceryl aminobenzoate, digalloyl trioleate and iscotrizinol; at a concentration in excess of 0.25% (wt).

11. The topical composition of claim 1, wherein the composition does not comprise any of the UVR filtering agents selected from the group consisting of allantoin-p-aminobenzoic acid complex, p-aminobenzoic acid, aluminium, phenylalanine, tryptophan, tyrosine, benzyl alcohol, 4-(2-hydroxyethyl)-1-piperazineethanesulfonic acid, carrot oil, camphor, clove oil, coenzyme Q10, coconut oil, methoxypropanediol, 5-(3,3-dimethyl-2-norbornadiene)-3-penten2-one, dipropylene glycol salicylate, eucalyptus leaf oil, glyceryl p-aminobenzoate, 2-hydroxy-1,4-naphthoquinone, magnesium aluminium silicate, microcrystalline titanium coated mica platelets, keratin, albumin, red petrolatum, shea butter, and tocopheryl acetate.

12. The topical composition of claim 1, wherein the composition further comprises a cosmetically or pharmaceutically acceptable carrier suitable for topical application selected from the group consisting of a lotion, a cream, a spray, a moisturizer, a gel, a lip balm, an insect repellent, a make-up, a water resistant agent, a penetration enhancer, an encapsulating agent, an emulsifying agent, a liquid solvent, an emollient, an organic chemical stabilizer, and mixtures thereof.

13. The topical composition of claim 1, wherein the composition is a sunscreen.

* * * * *